United States Patent [19]
Atkinson et al.

[11] Patent Number: 5,361,166
[45] Date of Patent: Nov. 1, 1994

[54] NEGATIVE ABBE NUMBER RADIAL GRADIENT INDEX RELAY AND USE OF SAME

[75] Inventors: Leland G. Atkinson, Rochester; Douglas S. Kindred, Springwater; Duncan T. Moore, Fairport; J. Robert Zinter, Rochester, all of N.Y.

[73] Assignee: Gradient Lens Corporation, Rochester, N.Y.

[21] Appl. No.: 17,034

[22] Filed: Jan. 28, 1993

[51] Int. Cl.$^5$ .............................. G01B 3/02
[52] U.S. Cl. ................................. 359/654
[58] Field of Search .................. 359/654, 655

[56] References Cited

U.S. PATENT DOCUMENTS

| | | |
|---|---|---|
| 3,257,902 | 6/1966 | Hopkins . |
| 3,626,194 | 12/1971 | Hirano et al. ............ 359/654 |
| 3,729,253 | 4/1973 | Moore et al. . |
| 3,827,785 | 8/1974 | Matsushita et al. ....... 359/654 |
| 3,936,149 | 2/1976 | Imai ........................ 359/654 |
| 4,515,444 | 5/1985 | Prescott et al. ........... 359/654 |
| 4,641,927 | 2/1987 | Prescott et al. ........... 359/654 |
| 4,648,221 | 8/1987 | Takada ..................... 359/654 |
| 4,723,843 | 2/1988 | Zobel . |
| 4,755,029 | 7/1988 | Okabe ...................... 359/654 |
| 4,770,506 | 9/1988 | Baba ........................ 359/654 |
| 5,182,672 | 1/1993 | Mukai et al. .............. 359/655 |

FOREIGN PATENT DOCUMENTS

| | | |
|---|---|---|
| 181727 | 5/1986 | European Pat. Off. ...... 359/654 |
| 2638999 | 3/1977 | Germany ................... 359/654 |
| 6354 | 1/1980 | Japan ....................... 359/654 |
| 5220 | 1/1986 | Japan ....................... 359/654 |

OTHER PUBLICATIONS

Refractive Index and Spectral Models for Gradient-Index Materials: Stephen D. Fantone.
Model for the Chromatic Properties of Gradient-Index Glass: Danette P. Ryan-Howard and Duncan T. Moore.
Gradient-index Optical Systems in Holographic Endoscopy G. von Vally, et al.
Correction of Chromatic Aberrations in GRIN Endoscopes: Dennis C. Leiner and Rochelle Prescott.
Development of New Gradient Index Glasses for Optical-Imaging Systems: Douglas Scott Kindred.
Design, Engineering, and Manufacturing Aspects of Gradient Index Optical Components: Stephen D. Fantone.

*Primary Examiner*—John T. Kwon
*Attorney, Agent, or Firm*—Cumpston & Shaw

[57] ABSTRACT

Radial gradient index of refraction (GRIN) optical relays are described for overcorrecting axial chromatic aberration. In particular, a relay including a negative dispersion radial GRIN rod alone or in combination with simple homogeneous or GRIN lenses is described for adjusting axial chromatic and monochromatic aberrations, including spherical, coma, astigmatism, and distortion. The invention also describes remote viewing scopes, such as endoscopes and borescopes, which utilize GRIN relays for achromatic, and reduced or corrected monochromatic aberration imaging The use of segmented GRIN relays provides a degree of flexibility in remote viewing scopes.

23 Claims, 4 Drawing Sheets

NEGATIVE ABBE NUMBER RADIAL GRADIENT INDEX RELAY AND USE OF SAME

BACKGROUND OF THE INVENTION

1. Field of the Invention

This invention relates generally to gradient index (GRIN) lenses, and specifically to the use of positive and negative Abbe number radial GRIN rod lenses as optical relays in endoscopes, borescopes, and similar type instruments.

2. Description of the Related Art

Endoscopes, borescopes, and similar type optical instruments, hereinafer referred to as "remote viewing scopes", are well known in the art for their use in viewing, through relatively small openings, body cavities and industrial vessels, for example, where direct viewing is not possible. A typical early scope instrument is described by Hopkins in U.S. Pat. No. 3,257,902. It employs a series of rod lenses forming an objective system and a relay system for forming and relaying the image of an object down a narrow tube to a camera.

Systems of this type typically undercorrect axial chromatic aberration due to the convex, or positive, refracting surfaces of the lenses which are necessary to converge light and form real images. The aberration appears as a halo around the image because the blue light components of the image are focused closer to the lens than the red components along the optical axis. Ideally, an image formed in white light would have a common focus for all wavelengths or colors and thus be a clear and true representation of the object being viewed.

Since classical optical elements having negative power, i.e. concave refracting surfaces, characteristically overcorrect axial color by focusing the red components closer to the lens than the blue components, axial chromatic aberration in the image formed by a Hopkins-type scope is correctable by appropriately using additional negative power lenses in the device. This approach, however, adds to complexity and cost, especially in view of the frequency of use and sterilization requirements of modern devices of this type. Leiner and Prescott, in *Applied Optics* 22, 3 p 383 (1983) also point to difficulties in manufacturing classical lenses of the required size and surface contours for use in scope-type instruments.

Around 1970, Nippon Sheet Glass (NSG) developed solid gradient index rod lenses for use in scope-type optical systems. An advantage of the NSG GRIN rods was their flat refracting surfaces. In addition, it was realized that light rays propagating through the lens follow a sinusoidal path having a defined period when the index gradient profile varies essentially parabolically as a function of the lens radius. The rod lens could then be cut to a design length corresponding to the periodicity of the light propagation path to achieve desired imaging results. Axial and radial gradient index lenses are now well known in the art. Moore et al. in U.S. Pat. No. 3,729,253, describe gradient index properties and cite references to the design and manufacture of GRIN rods used, for example, as image relays.

An inherent problem of all conventional lenses is the chromatic aberration created by dispersion of the lens material itself. Optical dispersion is the change in the index of refraction as a function of the wavelength of the light passing through the lens. In general, the refractive index of a material is larger in shorter wavelengths than in longer wavelengths. Thus, the index of refraction in blue light is greater than in red light. Positive dispersion, therefore, is responsible for undercorrected axial color in optical systems. Similarly, dispersion of a GRIN lens also contributes to axial chromatic aberration.

Thus, there is a need for GRIN components which characteristically overcorrect axial color, and which can be used to simplify the optical systems of scope-type instruments for color corrected imaging. It is therefore an object of this invention to use negative dispersion GRIN lenses in the optical systems of endoscopes and similar type instruments to reduce or eliminate axial chromatic aberration in the image.

It is a further object of the present invention to use negative dispersion GRIN rods in integral and/or optical combination with conventional optical components to reduce or eliminate spherical aberration and coma in addition to axial chromatic aberration in the image.

It is another object of this invention to use radial GRIN lenses in optical and/or integral combination with diffractive or holographic optical elements for axial chromatic aberration correction.

It is a still further object of the present invention to use a plurality of radial GRIN rod lens segments or sections in an endoscope, or like optical device, to give such devices a degree of physical flexibility in addition to corrected imaging capability.

SUMMARY OF THE INVENTION

The present invention uses negative dispersion radial gradient index rod lenses to overcorrect axial chromatic aberration in an image. The invention also uses negative dispersion radial GRIN rods in combination with undercorrecting axial color elements, and radial GRIN rods in combination with diffractive optical elements, in remote viewing scopes, for axial color and monochromatic aberration corrected imaging.

Dispersive characteristics of conventional, or homogeneous, optical materials used for imaging in visible light are defined, in part, by the homogeneous Abbe number ($V_{homo.}$) of the lens, expressed by $$V_{homo.} = (N_d - 1)/(N_F - N_C),$$

where $N_d$ is the material index of refraction for the helium d line (yellow light), and $N_F$ and $N_C$ are the indices of refraction for the hydrogen F line (blue light) and the hydrogen C (red light), respectively. The quantity $N_F - N_C$ is a measure of the dispersion of the material, while the Abbe number defines the dispersion relative to the amount of bending that a light ray undergoes in the material.

Every transparent material exhibits a higher index of refraction in blue than in red light (i.e., $N_F > N_C$), resulting in positive dispersion and undercorrected axial color. In contrast to a homogeneous optical element, however, the glass composition of a radial GRIN lens varies spatially as a function of lens radius, so that the Abbe number, as well as the index of refraction, also vary on a point-by-point basis with lens radius. In a radial GRIN lens the bending of the light depends on the refractive index of the lens material as well as on the change in refractive index with radius. Therefore, the chromatic aberration from a radial GRIN lens depends on the refractive index profile of the lens as well as on the dispersion of the base material. In further contrast to a homogeneous lens, the change in refractive index in a GRIN material can be larger in red light than in blue light, even though the absolute refractive index at any point in the material is larger in blue than in red light. In this case the GRIN material is said to have negative dispersion. Because the refractive index change determines the amount by which the light rays will be bent, a negative dispersion GRIN lens produces overcorrected axial chromatic aberration that can be used to compensate for undercorrected axial color arising from positive elements in an optical system.

The index of refraction profile for a radical GRIN material is expressed by $$N_\lambda(r) = N_{00,\lambda} + N_{10,\lambda} r^2 + N_{20,\lambda} r^4 + \ldots,$$

where r is the radical distance from the optical axis, and $N_{ij,\lambda}$ are constants which describe the index gradient at a particular wavelength. A radical gradient Abbe number ($V_{10}$) is defined by $$V_{10} = N_{10,d}/(N_{10,F} - N_{10,C}).$$

When the coefficient $N_{10}$ has an absolute value that is greater in the blue (F line) than in the red (C line) portion of the spectrum, the value of $V_{10}$ is positive and acts like the positive Abbe number of a homogeneous lens. In the gradient index case, on the other hand, when $N_{10}$ is greater in absolute value in red light than in blue light, $V_{10}$ is negative, and the lens is said to have negative dispersion. Since homogeneous lenses cannot exhibit negative Abbe values, a principal advantage in axial color correction from negative dispersion GRIN materials is recognized.

The invention thus discloses the use of negative Abbe number GRIN relays which overcorrect axial chromatic aberration in remote viewing scopes and which use results in reduced or absent axial chromatic aberration in the final image. The properties of negative Abbe value GRIN lenses have been thoroughly modeled and the manufacture of glass materials having radial index gradients is known to those skilled in the art. Such design and manufacturing techniques are described, for example, by Fantone, *Design, Engineering and Manufacturing Aspects of Gradient Index Optical Components,* PhD Thesis, The Institute of Optics, University of Rochester, New York (1979); Fantone, *Refractive Index and Spectral Models for Gradient-Index Materials,* Applied Optics 22, 3 p. 432 (1983); Ryan-Howard and Moore, *Model for the Chromatic Properties of Gradient Index Glass,* Applied Optics 24, 24 p. 4356 (1985); and Kindred, *Development of New Gradient Index Glasses For Optical Imaging Systems,* PhD Thesis, The Institute of Optics, University of Rochester, New York (1990). Kindred actually produced an optical component consisting of a thin slab of material having a radial gradient index and a net negative Abbe number that was capable of image formation when immersed in an index matching liquid; however, negative Abbe number radial GRIN relays, in particular, are not previously described by those skilled in the art.

The present invention describes novel uses and applications of radial gradient index rod lenses. The invention further discloses the use of negative Abbe value radical GRIN rod lenses with variable combinations of planar and non-planar refracting surfaces for monochromatic aberration adjustments as well as achromatic imaging. Non-planar refractive GRIN rod surfaces are achieved by attaching, or optically combining, homogeneous or GRIN non-plano-plano elements and the GRIN rods. GRIN rods can also be combined with holographic or diffractive optical elements to produce specific amounts of over- or undercorrected axial chromatic aberration in addition to reducing spherical aberration and coma. Furthermore, spherical aberration and coma from a GRIN lens can be reduced by adjusting the fourth and higher order expansion terms of the radical gradient index of refraction, as is well known by those skilled in the art.

The invention further discloses optical relays in remote viewing scopes comprising positive and negative Abbe number radical GRIN rods in which the rods are cut into segments for adding limited flexibility to a normally rigid orthopedic endoscope, for example. In this case, the rods are cut into lengths such that no intermediate images are formed by any lens/air interface of the relay system. Light rays follow a sinusoidal path through the GRIN rod of the invention, in which the pitch, $P_\lambda$, of the lens, or equivalently, the period of the sinusoidal light path, is described by $$P_\lambda = 2\pi \sqrt{N_{00,\lambda}/-2N_{10,\lambda}}$$

As intermediate images are formed at every half-period distance, a paraxial axial ray will attain its greatest amplitude at every first and third one-quarter pitch point ($P_\lambda/4$) of the lens when the image initially falls on the first face of the GRIN rod; the one-quarter pitch point being expressed by $$P_\lambda/4 = \pi/2 \sqrt{N_{00,\lambda}/-2N_{10,\lambda}}$$

The invention also describes segmented negative dispersion radial GRIN rods for use in remote viewing scope relay systems wherein baffles are located slightly to the object side of selected one-quarter pitch positions for reducing scatter from off-axis illumination vignetted by the rod lens.

BRIEF DESCRIPTION OF THE DRAWINGS

FIG. 7 also shows the sinusoidal light path that light takes as it propagates through the GRIN rod;

DETAILED DESCRIPTION OF THE INVENTION

Figure 1:
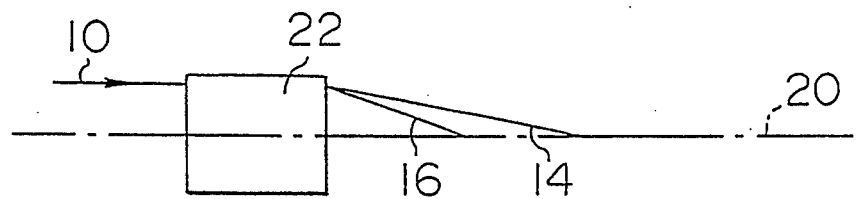
FIG. 1 is a line drawing of a negative dispersion optical element.

Having described the various objects, advantages, and applications of the present invention, reference is now made to the drawings in which FIG. 1 shows a diagrammatic illustration of a negative dispersion, negative Abbe number radial GRIN element 22 which focuses the red component 16 of the incident white light 10 nearer the lens than the blue component 14 along optical axis 20; the lens overcorrects axial chromatic aberration.

Figure 2:
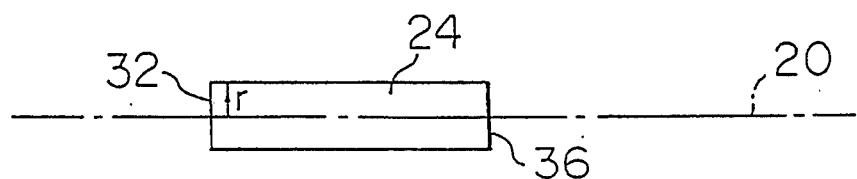
FIG. 2 shows a negative Abbe number radial GRIN rod having plane parallel end faces normal to the optical axis.
Figure 3A:
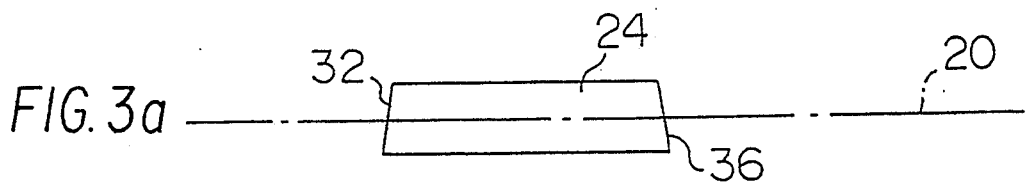
FIGS. 3(a)–(d) show the GRIN rod of FIG. 2 having various end face contours for adjusting selected monochromatic aberrations.
Figure 3B:
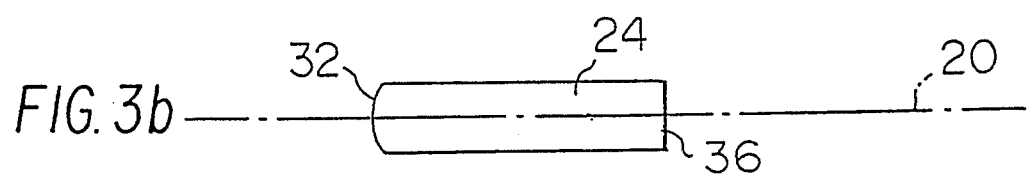
Figure 3C:
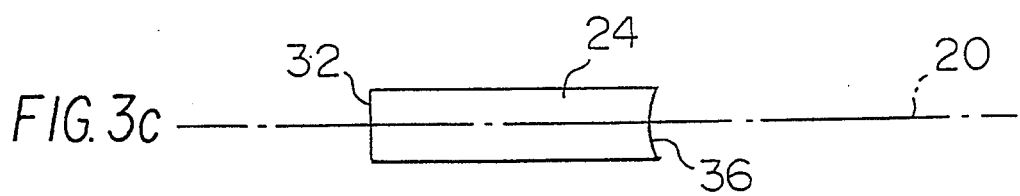
Figure 3D:
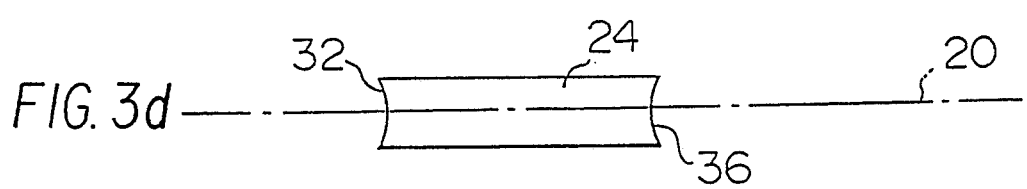

A preferred embodiment of the present invention is shown in FIG. 2 in which the negative Abbe number radial GRIN component is a rod lens 24 having an essentially parabolic variation of refractive index as a function of lens radius r, described by the expression $$N_\lambda(r) = N_{00,\lambda} + N_{10,\lambda} r^2 + N_{20,\lambda} r^4 + N_{30,\lambda} r^6 + \ldots,$$

where $N_{00,\lambda}$ is the base refractive index of the material and $N_{ij,\lambda}$ are constants which describe the index gradient at a particular wavelength $\lambda$. In particular, $N_{10,\lambda}$ relates to the period $P_\lambda$ of the sinusoidal propagation of light through the lens, defined by $$P_\lambda = 2\pi \sqrt{N_{00,\lambda}/-2N_{10,\lambda}};$$

while the higher order index terms provide adjustment for monochromatic aberrations such as spherical aberration and coma.

In addition to overcorrecting axial color with a negative Abbe number radial GRIN material exhibiting negative dispersion, monochromatic aberrations, like spherical aberration and coma, can also be reduced or eliminated by the selective combination of curvatures of the GRIN rod end faces.

FIG. 3 diagrammatically illustrates four examples of GRIN rod 24 having variously contoured first and second end faces, 32, 36. Specifically, FIG. 3(a) shows GRIN rod 24 with planar faces 32, 36 not normal to optical axis 20. FIG. 3(b) shows a spherical-convex first face 32 and a plano rear face 36 on GRIN rod 24. FIG. 3(c) shows GRIN rod 24 with plano front face 32 and spherical-concave rear face 36; while FIG. 3(d) shows the GRIN rod having aspheric-concave front and rear faces 32, 36. It is to be understood that this embodiment of the invention is not limited only to the combinations shown but comprises all combinations of surface contours, including bi-convex and bi-concave.

Figure 4:
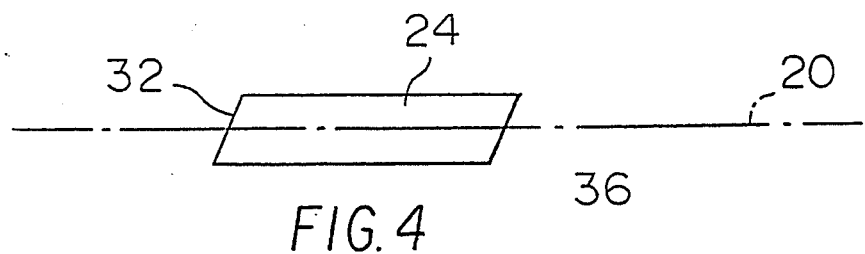
FIG. 4 is a line drawing of the rod lens of FIG. 2 in which the plane parallel end faces are not normal to the optical axis.

FIG. 4 shows another embodiment of the invention in which negative Abbe number GRIN rod 24 has plane parallel faces 32, 36 which are not normal to the optical axis 20. Further, as shown in FIG. 2, surfaces 32, 36 are plane parallel and normal to optical axis 20.

Figure 5:
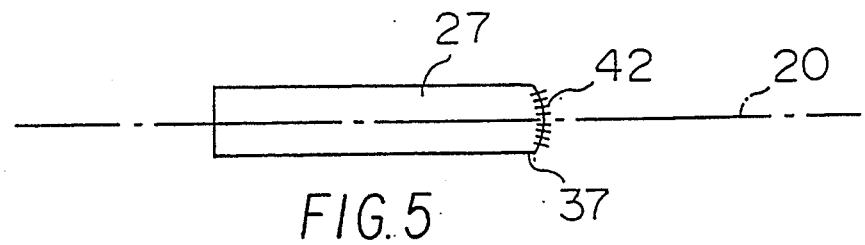
FIG. 5 is a line drawing of a positive dispersion radial GRIN rod having a holographic optic attached to one of the end faces for overcorrecting axial chromatic aberration.

It is well known in the art that diffractive, or holographic, optical elements characteristically overcorrect axial color. FIG. 5 shows an embodiment of the present invention in which a holographic optical element ("HOE") 42 is attached to the rear face 37 or radial GRIN rod 26. HOE 42 significantly overcorrects axial chromatic aberration and so is able to compensate for the undercorrected axial color characteristic of positive, or homogeneous, Abbe number optical elements typically found in remote viewing scopes. It is to be understood that the HOE need not be physically connected to the GRIN rod; equivalent overcorrection is achieved when the HOE is in direct optical contact with the GRIN rod.

Figure 6A:
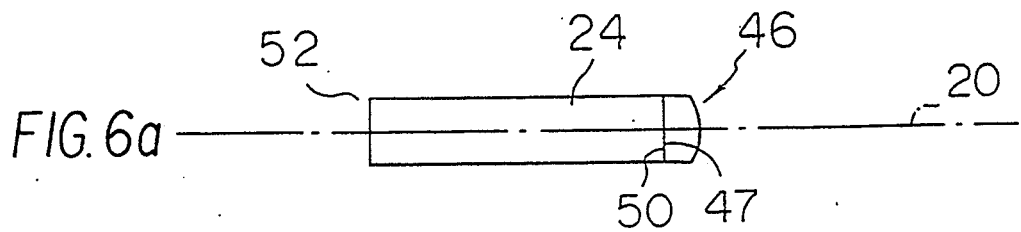
FIGS. 6(a) and 6(b) are line drawings of the negative Abbe number radial GRIN rod of FIG. 2 with separate homogeneous and GRIN elements, respectively, attached to the rod lens for axial chromatic and monochromatic aberration adjustment.
Figure 6B:
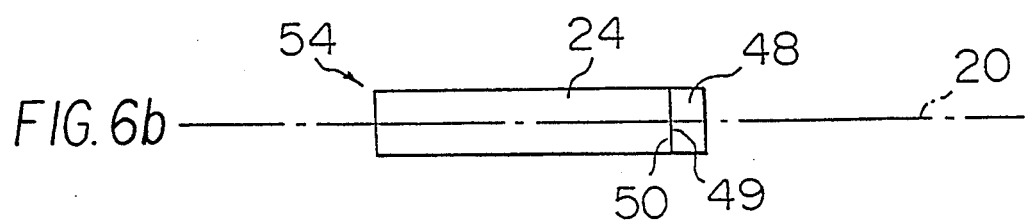

In another embodiment of the present invention, as seen in FIGS. 6(a) and 6(b), simple homogeneous lens 46 and gradient index lens 48, respectively, are combined with negative Abbe number GRIN rod 24 to form lenses 52, 54, respectively. Lens 46 and GRIN lens 48 each have at least one planar surface 47, and 49, respectively, which form the boundary of attachment to planar face 50 of GRIN rod 24. Lenses 46, 48 are used to adjust certain monochromatic aberrations such as spherical aberration and coma, for example, and when one of the lens combinations 52, 54 are used in a remote viewing scope, the final image is color corrected and has reduced spherical aberration and coma.

Figure 7:
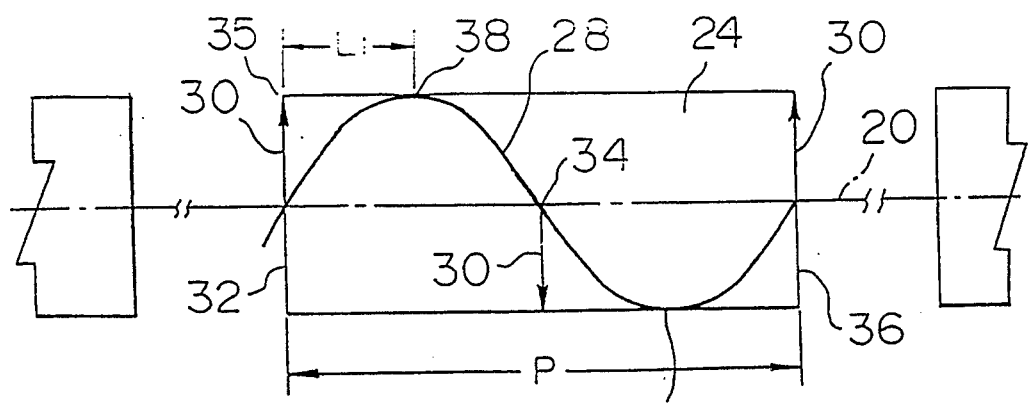
FIG. 7 is a line drawing of an optical relay having at least one negative Abbe number GRIN rod as shown in FIG. 2.

FIG. 7 shows an embodiment of the invention in which an optical relay 35 comprises at least one negative Abbe number radial GRIN rod 24. FIG. 7 particularly shows one full period $P_\lambda$ of the sinusoidal path of an on-axis axial ray 28 as it propagates through lens 24. As drawn, intermediate image 30 is formed on the front face 32 of negative Abbe number GRIN rod 24; at location 34 where axial ray 28 crosses optical axis 20; and on the rear face 36 of the lens. In this case, $L_1$ represents a one-quarter pitch length $P_\lambda/4$; i.e., location 38 represents the position in lens 24 where ray 28 would exit the lens collimated if the lens was cut at that location. Likewise, location 40 shows the third one-quarter pitch position of lens 24.

Figure 8:
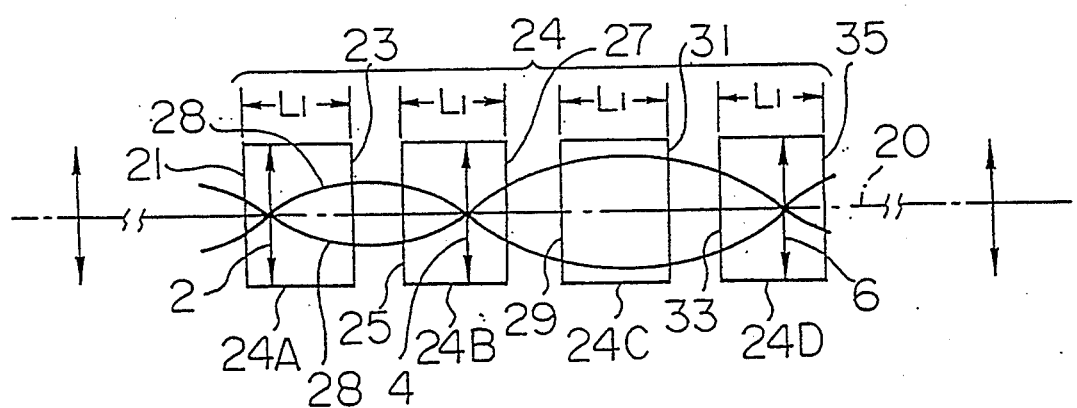
FIG. 8 is a line drawing of a negative Abbe number GRIN rod of FIG. 2 which has been cut into segments that a remote viewing scope that incorporates the segmented relay would have limited flexibility. A ray path through the lens segments illustrates intermediate image formation.

In one embodiment of the invention, shown in FIG. 8, GRIN rod 24, comprising the relay of an orthopedic endoscope (not shown), is cut into segments 24A, 24B, 24C, and 24D to give the instrument slightly increased flexibility. Each section has a length such that intermediate images 2, 4, and 6 are formed intermediate the segment end faces 21, 23; 25, 27; 29, 31; and 33, 35 as illustrated by the intersection of the axial rays 28 with the optical axis 20.

Figure 9:
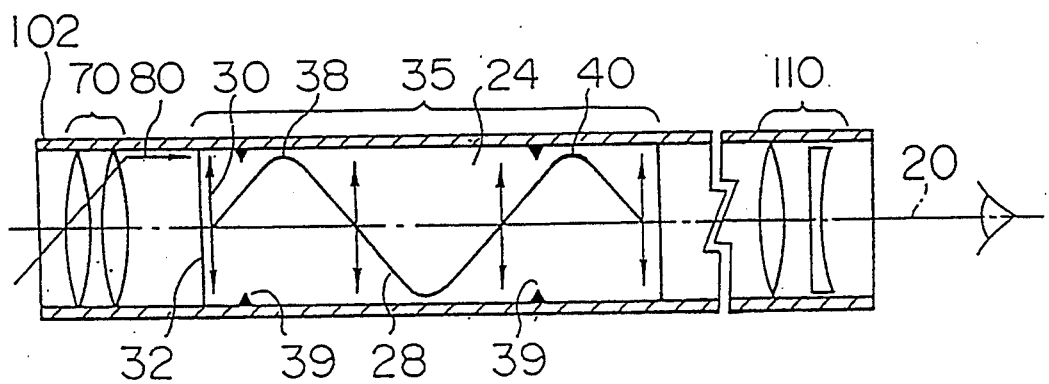
FIG. 9 diagrammatically illustrates, in cross section, a remote viewing scope including a housing and an objective system, a GRIN rod relay, and a viewing system disposed therein. For the sake of clarity, the internal lenses are not shown in cross section.

FIG. 9 shows a preferred embodiment of the invention in which an objective system 70, a relay 35, and a viewing system 110 are aligned and disposed within an endoscope housing 102. Objective group 70 is telecentric to relay system 35. In this case, marginal ray 80 from the object enters the negative Abbe number radial GRIN relay rod 24 parallel to the optical axis 20 and follows a sinusoidal path 28 through the lens as shown. The telecentric embodiment comprises at least a two element objective group 70 for increased field of view over a single objective lens. In a non-telecentric arrangement, the chief ray from the object does not enter the first GRIN relay lens parallel to the optical axis resulting in clipping of the sinusoidally transmitted light and increased scatter through the system, or the need for a relay with a larger numerical aperture. It follows from this, and with reference to FIG. 9, that when intermediate image 30 is formed on front surface 32 of GRIN rod 24, a baffle 39 located at the first and third one-quarter pitch locations 38, 40, respectively, would effectively reduce optical noise at the points of maximum axial ray height in the rod from propagating through the system. When the rays entering the relay are non-telecentric, vignetting occurs ahead or in front of the quarter-pitch locations. For this reason, baffle 39 is positioned slightly to the object side of one-quarter pitch points 38, 40, as shown in FIG. 9.

Figure 10:
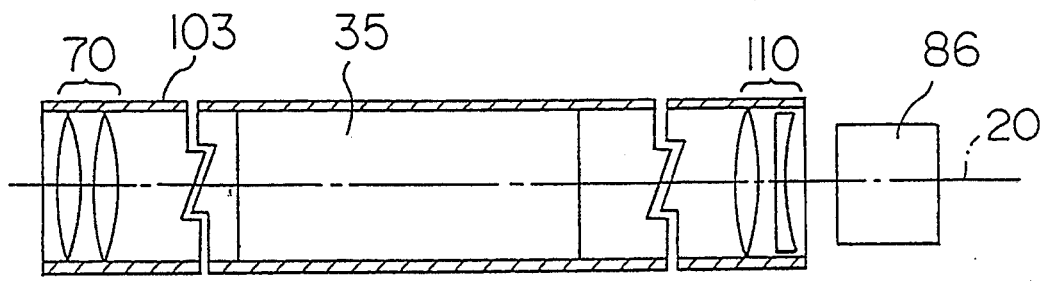
FIG. 10 shows the remote viewing scope of FIG. 9 wherein the viewer's eye is replaced by an electronic imaging sensor.

In FIG. 10, image sensing means 86, including conventional optical and electronic means, are used in combination with the viewing system 110, and in place of a viewer's eye. In this embodiment, objective system 70, relay 35, and viewing system 110 are disposed within borescope housing 103, while image sensing means 86 remains separated from the remote viewing scope.

Figure 11:
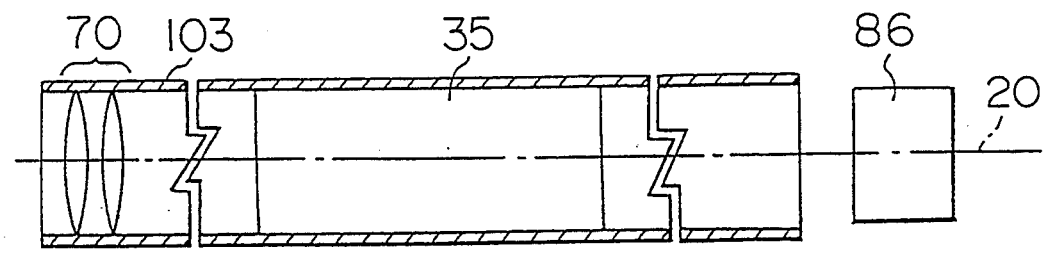
FIG. 11 shows the remote viewing scope of FIG. 10 in which an electronic imaging sensor is used without an eye piece group.

FIG. 11 shows a further embodiment of the invention in which the image sensing means 86 is used in combination with a remote viewing scope having no eyepiece 110; i.e., the image from the relay falls directly on the image sensing means 86. It is to be understood that the remote viewing scope comprising an eyepiece 110 designed for viewing the image with the eye, or by electrical or optical means alone, or the eyepiece/sensing means combination, are all embodiments of the remote viewing scope of the invention.

Figure 12:
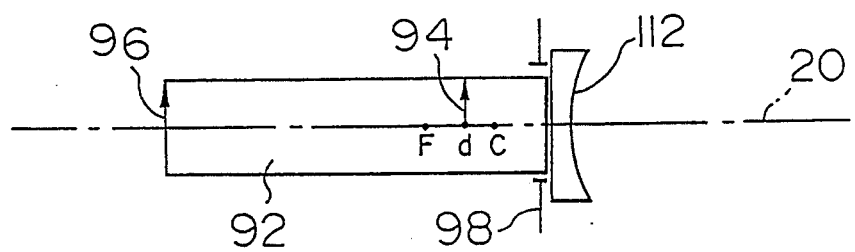
FIG. 12 is a line drawing of the prior art showing axial chromatic aberration correction by a positive Abbe number GRIN rod and a negative power homogeneous lens attached thereto.

Finally, FIG. 12 illustrates a prior art device for correcting axial chromatic aberration wherein a homogeneous plano-concave lens 112 is combined with a positive Abbe number GRIN rod 114. The axial chromatic color is corrected by forming a virtual image 94 of object 96 in front of the exit pupil 98 of the system.

Although specific embodiments of the invention have been disclosed, it will be understood that the invention is not limited to the details of the foregoing constructions, which are merely exemplary, and which more clearly appear in the following appended claims.

What is claimed is:

1. An optical relay for propagating an image along an optical axis comprising:
   at least one radial GRIN component having a negative Abbe number, for reducing undercorrected axial chromatic aberration.

2. The optical relay of claim 1 in which the at least one radial GRIN component comprises a rod lens having an axial dimension greater than its diameter.

3. The optical relay of claim 2 in which the at least one radial GRIN component has an Abbe value in the range from negative infinity to −50.

4. The optical relay of claim 2 in which the at least one rod lens comprises a plurality of rod lens segments, each segment having a pair of end faces, each segment further having a length such that each of a plurality of intermediate images propagating through the rod lens segments are formed intermediate the end faces of each lens segment.

5. The optical relay of claim 2 in which the at least one rod lens comprises a first end face and a second end face, each end face having a contour selected from the group consisting of:
   planar;
   spherical convex;
   spherical concave; and,
   aspherical.

6. The optical relay of claim 5 in which the end faces are plane parallel.

7. The optical relay of claim 6 in which the end faces are normal to an optical axis through the lens.

8. An optical relay, comprising:
   a radial GRIN component having a negative Abbe number for reducing undercorrected axial chromatic aberration; and
   a baffle for reducing scattered illumination in the relay located slightly to the object side of a one one-quarter pitch point of the GRIN component.

9. The optical relay of claim 8 in which the one-quarter pitch points are disposed at distances, nL, from the object end of the lens, where:

$$L = \pi/2 \sqrt{N_{00,\lambda}/-2N_{10,\lambda}};$$

where $N_{00,\lambda}$ is the base index of refraction of the GRIN rod at wavelength $\lambda$, $N_{10,\lambda}$ is a gradient index constant at wavelength $\lambda$, and n is an integer.

10. An optical component for overcorrecting axial chromatic aberration and reducing at least one of spherical aberration, coma, astigmatism, and distortion comprising:
   a negative Abbe number radial GRIN rod having a first planar end face and a second planar end face;
   a lens having one of a plano-convex shape, a plano-concave shape, and a plano-aspheric shape;
   the lens being attached to at least one of the first and second end faces of the GRIN rod.

11. The optical component of claim 10 in which the GRIN rod has an Abbe number in the range between negative infinity and −50.

12. The optical component of claim 10 in which the lens has a radial gradient index of refraction.

13. A remote viewing scope comprising:
   a housing, and an optical system disposed therein including:
   an objective system; and
   a relay comprising at least one radial GRIN component having a negative Abbe number, aligned with the objective system.

14. The remote viewing scope of claim 13 in which the at least one radial GRIN component comprises a rod lens having an axial dimension greater than the its diameter.

15. The remote viewing scope of claim 13 in which the at least one radial GRIN component has an Abbe value in the range between negative infinity and −50.

16. The remote viewing scope of claim 13 in which the objective system is telecentric to the relay.

17. The remote viewing scope of claim 13 further comprising an eyepiece group aligned to the relay.

18. An optical relay according to claim 1 in which the relay is symmetrical along its optical axis.

19. The optical relay of claim 18 in which the at least one radial GRIN component comprises a rod lens having an axial dimension greater than its diameter.

20. The optical relay of claim 19 in which the at least one radial GRIN component has an Abbe value in the range from negative infinity to −50.

21. The optical relay of claim 19 in which the at least one rod lens comprises a first end face and a second end face, each end face having a contour selected from the group consisting of:
  planar;
  spherical convex;
  spherical concave; and
  aspherical.

22. The optical relay of claim 21 in which the end faces are plane parallel.

23. The optical relay of claim 22 in which the end faces are normal to an optical axis through the lens.

* * * * *

UNITED STATES PATENT AND TRADEMARK OFFICE
CERTIFICATE OF CORRECTION

PATENT NO. : 5,361,166
DATED : November 1, 1994
INVENTOR(S) : Leland G. Atkinson, Douglas S. Kindred, Duncan T. Moore
Robert Zinter It is certified that error appears in the above-indentified patent and that said Letters Patent is hereby corrected as shown below:

Column 3, line 12, please delete "radical" and insert -- radial --.
Column 3, line 17, please delete "radical" and insert -- radial --.
Column 3, line 19, please delete "radical" and insert -- radial --.
Column 3, line 64, please delete "radical" and insert -- radial --.
Column 4, line 13, please delete "radical" and insert -- radial --.
Column 4, line 9, please delete "radical" and insert -- radial --.

Signed and Sealed this

Seventeenth Day of October, 1995

Attest:

BRUCE LEHMAN

*Attesting Officer*     *Commissioner of Patents and Trademarks*